(12) United States Patent
Al-Qudah et al.

(10) Patent No.: US 12,349,947 B2
(45) Date of Patent: Jul. 8, 2025

(54) DISTAL-SCREW GUIDING SYSTEM FOR INTERLOCKING INTRAMEDULLARY NAIL IMPLANTS

(71) Applicants: WESTERN WASHINGTON UNIVERSITY, Bellingham, WA (US); Ala' K. Al-Qudah, Irbid (JO)

(72) Inventors: Sura Al-Qudah, Bellingham, WA (US); Ala' K. Al-Qudah, Irbid (JO); Levi Smith, Olympia, WA (US)

(73) Assignee: Western Washington University, Bellingham, WA (US)

( * ) Notice: Subject to any disclaimer, the term of this patent is extended or adjusted under 35 U.S.C. 154(b) by 0 days.

(21) Appl. No.: 18/046,800

(22) Filed: Oct. 14, 2022

(65) Prior Publication Data

US 2024/0122631 A1    Apr. 18, 2024

Related U.S. Application Data

(60) Provisional application No. 63/255,823, filed on Oct. 14, 2021.

(51) Int. Cl.
*A61B 17/72* (2006.01)
*A61B 17/17* (2006.01)

(52) U.S. Cl.
CPC .......... *A61B 17/72* (2013.01); *A61B 17/1725* (2013.01)

(58) Field of Classification Search
CPC ................. A61B 17/1725; A61B 17/72–7291
See application file for complete search history.

(56) References Cited

U.S. PATENT DOCUMENTS

| | | | | |
|---|---|---|---|---|
| 9,155,582 B2 * | 10/2015 | Felder | ................ | A61B 17/1721 |
| 2005/0085825 A1 * | 4/2005 | Castaneda | .......... | A61B 17/1725 606/102 |
| 2006/0030859 A1 * | 2/2006 | Gotfried | ............ | A61B 17/1725 606/99 |
| 2006/0189996 A1 * | 8/2006 | Orbay | ................ | A61B 17/1717 606/87 |
| 2006/0271056 A1 * | 11/2006 | Terrill-Grisoni | .... | A61B 17/1675 606/84 |
| 2009/0062796 A1 * | 3/2009 | Parks | ..................... | A61B 17/72 606/62 |
| 2009/0157077 A1 * | 6/2009 | Larsen | ................ | A61B 17/1725 606/62 |
| 2010/0211073 A1 * | 8/2010 | Merrell | .................. | A61B 17/72 606/62 |
| 2017/0164992 A1 * | 6/2017 | Dassonville | ....... | A61B 17/8872 |
| 2019/0343569 A1 * | 11/2019 | Hedgeland | ......... | A61B 17/1725 |
| 2020/0029980 A1 * | 1/2020 | Dutoit | ................ | A61B 17/1725 |
| 2020/0155211 A1 * | 5/2020 | Vicenzi | ............. | A61B 17/1725 |
| 2020/0253649 A1 * | 8/2020 | Langdale | ........... | A61B 17/0401 |

(Continued)

*Primary Examiner* — Eduardo C Robert
*Assistant Examiner* — Steven J Cotroneo
(74) *Attorney, Agent, or Firm* — CHRISTENSON O'CONNOR JOHNSON KINDNESS PLLC

(57) ABSTRACT

A screw locating system including an intramedullary nail, a locating hole at the distal end of the intramedullary nail, a locator pin including a hollow section, and a locating end configured to fit in the locating hole, a cap configured to fill in the locating hole when the locator pin is in the locating hole, a screw configured to securely hold the locator pin, and a jig configured to guide a user to locate at least one distal screw at the distal end of the intramedullary nail.

19 Claims, 4 Drawing Sheets

(56) References Cited

U.S. PATENT DOCUMENTS

2021/0248779 A1\* 8/2021 Blau .......................... G06T 7/75
2021/0346075 A1\* 11/2021 Daly ................... A61B 17/7241
2022/0202464 A1\* 6/2022 Rossney ............. A61B 17/8605
2022/0287743 A1\* 9/2022 Orbay .................... A61B 17/72

\* cited by examiner

US 12,349,947 B2

DISTAL-SCREW GUIDING SYSTEM FOR INTERLOCKING INTRAMEDULLARY NAIL IMPLANTS

CROSS REFERENCE TO RELATED APPLICATION

This application claims the benefit of U.S. Provisional Application 63/255,823, filed Oct. 14, 2021, the entire disclosure of which is hereby incorporated by reference.

BACKGROUND

The interlocking intramedullary nail implant is used in cases of fractures that require stabilization using screws on both the proximal and distal ends of the bone. The nail is inserted through the center of the bone, where it can be secured via holes for screws located near the proximal and distal ends. The implant is used in a variety of locations including femoral, tibial, and humeral applications.

There are several existing designs for locating apparatus for interlocking intramedullary nails. However, while these devices work in theory, they are frequently unwieldy in practice and are insufficient for locating the screws on the distal end of the intramedullary nail. While existing distal screw locating methods do effectively reduce the radiation exposure to the surgeon below governmental regulations for radiation exposure, the number of x-rays performed is still a cause for concern and limits the number of these procedures that can be performed safely. Additionally, none of the designs adequately account for the issue of the implant bending during insertion. Due to this deflection issue, methods of performing the procedure without any guiding method are frequently relied upon, increasing the radiation exposure issue.

The method of locating from the proximal end is particularly vulnerable to this deflection. Additionally, any slight angular misalignment on the proximal end will be significantly amplified as the device reaches toward the distal end resulting in the guide being off by several millimeters. This flaw in design results in surgeons needing to locate each screw hole individually requiring a lengthy process involving several x-rays. The number of x-rays required for a single procedure causes significant radiation exposure for medical personnel. This poses a health risk to medical staff and limits the number of procedures as a safety measure. As such, systems and methods are needed to remedy this issue.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, a screw locating system including an intramedullary nail, a locating hole at the distal end of the intramedullary nail, a locator pin comprised of a hollow section and a locating end configured to fit into the locating hole, a cap configured to fill in the locating hole when the locator pin is in the locating hole, a screw configured to securely hold the locator pin, and a jig configured to guide a user to locate at least one screw at the distal end of the intramedullary nail is disclosed.

In another aspect, a method for locating distal screws comprising placing a intramedullary nail with a locating hole into a bone, visualizing the locating hole with an x-ray, drilling a pilot hole through the bone into a small section of the locating hole, inserting a locator pin with a hollow section into the locating hole, inserting a screw into the hollow section of the locator pin so that it slides into the bottom of the locator pin, tightening the screw so that the locator pin is attached to the intramedullary nail, placing a jig onto the locator pin, and locating at least one distal screw with the jig is disclosed.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
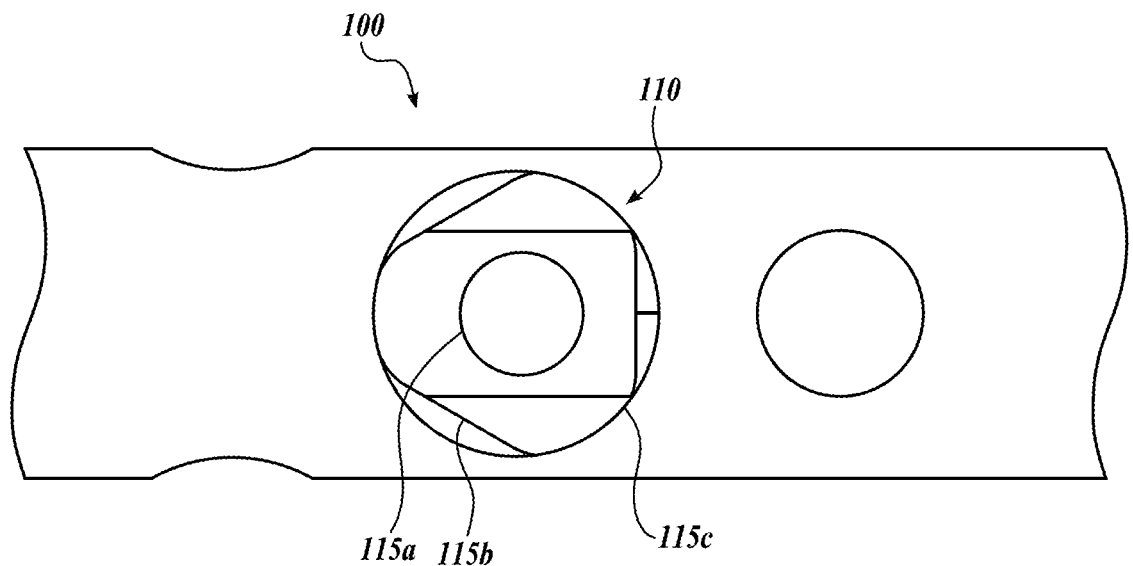
FIG. 1 is a front view of an example intramedullary nail in accordance with the present technology.

While illustrative embodiments have been illustrated and described, it will be appreciated that various changes can be made therein without departing from the spirit and scope of the invention.

In one aspect, a screw locating system including an intramedullary nail, a locating hole at the distal end of the intramedullary nail, a locator pin comprised of a hollow section and a locating end configured to fit into the locating hole, a cap configured to fill in the locating hole when the locator pin is in the locating hole, a screw configured to securely hold the locator pin, and a jig configured to guide a user to locate at least one screw at the distal end of the intramedullary nail is disclosed.

In some embodiments, the locating hole includes a first section, a second section, and a third section.

In some embodiments, the first section of the locating hole is a threaded hole through the intramedullary nail. In some embodiments, the threaded hole through the intramedullary nail is through the backside of the intramedullary nail. In some embodiments, the first section of the locating hole is a 3 mm threaded hole.

In some embodiments, the second section is a hole that extends into the midplane of the intramedullary nail. In some embodiments the second section is triangular shaped.

In some embodiments, the third section is a hole that extends into the intramedullary nail so that the profile of the second section is on a completely flat surface. In some embodiments, the third section is circular.

In some embodiments, the screw has a domed head. In some embodiments, the screw has a domed head such that it has a 4 mm radius of curvature.

In some embodiments, the cap is identical in shape to the locating end of the locator pin. In some embodiments, the cap is shaped to match the diameter of the intramedullary nail.

In some embodiments, the intramedullary nail is a tibial nail. In some embodiments, the intramedullary nail is a humeral nail. In some embodiments, the intramedullary nail is a femoral nail.

In another aspect, a method for locating distal screws comprising placing a intramedullary nail with a locating hole into a bone, visualizing the locating hole with an x-ray, drilling a pilot hole through the bone into a small section of the locating hole, inserting a locator pin with a hollow section into the locating hole, inserting a screw into the hollow section of the locator pin so that it slides into the bottom of the locator pin, tightening the screw so that the locator pin is attached to the intramedullary nail, placing a jig onto the locator pin, and locating at least one distal screw with the jig is disclosed.

In some embodiments, the locating hole is comprised of a first section, a second section, and a third section. In some embodiments, the second section of the locating hole is a hole that extends into the midplane of the intramedullary nail. In some embodiments, the second section of the locating hole is triangular.

In some embodiments, the locator pin has a locating end. In some embodiments, the locating end is triangular.

In some embodiments, the method further includes orienting one of the points of the triangular locating end of the locator pin towards the proximal end of the locator pin.

In some embodiments, the method further includes rotating the locator pin until it seats fully into the locating hole.

The system is composed of at least five components outlined below. The system includes 1) a specially shaped locating hole in the distal end of the intramedullary nail, 2) a specially shaped hollow pin that fits securely into the locating hole, 3) a cap designed to fill in the locating hole when the procedure is complete, 4) a screw designed to securely hold the locating pin, 5) and a jig that is securely located using the locating pin that guides the surgeon to locate the screws in the distal end of the nail. By locating much closer to the distal screws the deflection issue that is encountered by other methods is effectively avoided, and the issues with minor misalignments are no longer of such great significance.

Once the nail is in place, the locating hole can be located using an x-ray. After the hole is located, the surgeon can drill a small pilot hole through the bone into the small section of the locating hole, stopping before drilling through the rear side of the bone. Once the hole is started, a guidewire can be inserted so that a cannulated drill bit with a 7 mm diameter can be used to precisely clear the way to the locating hole for the locating pin. At this point the locating pin can be inserted into the locating hole; one of the points of the triangular section should be oriented towards the proximal end. The locating pin should be rotated slightly until it seats fully into the locating hole. The screw can then be inserted into the hollow section of the locator pin, and it should slide to the bottom of the pin and then should be tightened carefully so that the locator pin is securely attached to the nail. Once this is complete the guide jig can be placed onto the locator pin. The jig can then be seated fully on the bottom of the triangular section of the pin and secure it in place with a small set screw. The jig may now be used to locate the distal screws. When the screws are in place the jig may be removed. The screw should be loosened from the locator pin allowing for the locator pin to be removed. The pin should then be replaced by the locator hole cap and secured in the same method as the pin.

FIG. 1 is a front view of an example intramedullary nail in accordance with the present technology. An intramedullary nail 100 includes a locating hole 110, which consists of three main sections that are critical to the design. In some embodiments, these sections are a first section 115a, a second section 115b, and a third section 115c. The first section 115a may be a threaded hole through the intramedullary nail 100. In some embodiments, the threaded hole is through the backside of the intramedullary nail. In some embodiments, the first section 115a is a 3 mm threaded hole. In some embodiments, the first section 115a is the only section that engages with the screw allowing the screw to provide significant clamping force giving a very secure fit. In some embodiments, the second section 115b is a hole that extends to the midplane of the intramedullary nail 100. In some embodiments, such as the one illustrated in FIG. 1, the second section 115b is a triangular shaped hole, but it may take the form of many different shapes, such as diamond or hexagonal. The purpose of the second section 115b is to ensure the proper orientation and constrain the rotation of the locating pin. The third section 115c may be a section that extends just deep enough that the profile of the second section 115b is on a completely flat surface and is not distorted by the curved surface of the intramedullary nail 100. In some embodiments, the third section 115c is circular. In some embodiments, the third section 115c is 7 mm in diameter. This is necessary so that the 7 mm diameter channel can be drilled through the bone fully clearing the locating hole such that the locating pin can be easily inserted.

Figure 2:
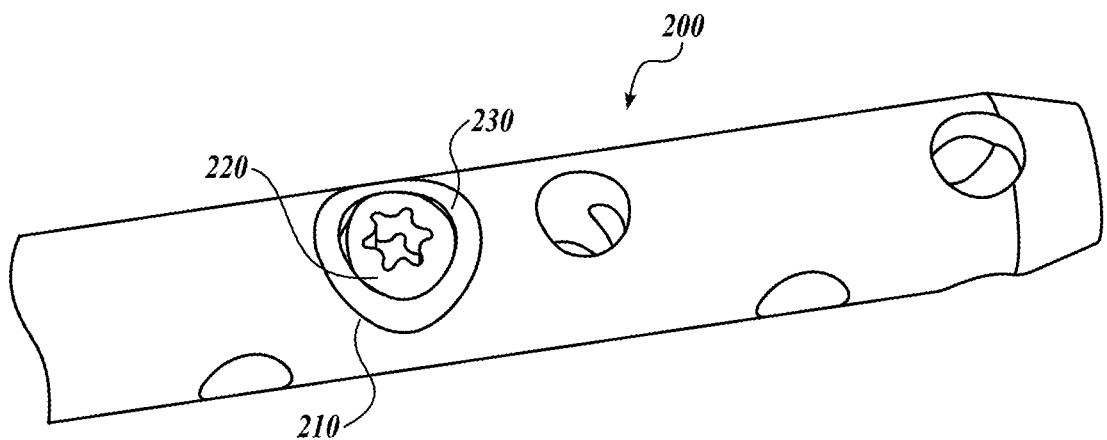
FIG. 2 is an isometric view of an example intramedullary nail in accordance with the present technology.

FIG. 2 is an isometric view of an example intramedullary nail 200 in accordance with the present technology. Intramedullary nail 200 may include a locating hole 210, a screw 220, and a locating hole cap 230.

In some embodiments, the intramedullary nail 200 is a tibial nail. In some embodiments, the intramedullary nail 200 is a femoral nail. In some embodiments, the intramedullary nail 200 is a humeral nail.

The screw 220, may be specially designed to work in this system and it serves the purpose of securing either the locating pin or the locating hole cap. In operation, the screw 220 threads into the small hole in the back side of the intramedullary nail 200 applying clamping pressure via the head. This screw system may use the same torx drive system that is used in existing systems, specifically size T10 approximately 2.74 mm, which does an excellent job of preventing cam out and stripping when driving the screw. Care may need to be taken to avoid overtightening or damaging the threads for this precaution a torque limiting screwdriver should be used limiting the applied torque to less than 3.4 Nm. The last key feature of the screw 220 is that the head is domed such that it has a 4 mm radius of curvature. This is a critical feature because it allows for the screw to sit fully under the level of the cap allowing the bone to heal generally with minimal ingress into the intramedullary nail implant. Additionally, this allows for removing the implant without needing to first remove the locating screw.

The locating hole cap 230 is illustrated as installed in FIG. 2 and is designed to fill in the locating hole preserving the rigidity of the intramedullary nail 200 and preventing ingress of the bone as it heals. In some embodiments, the cap is identical in shape to the locating end of the locating pin (as pictured in FIGS. 3A-3B) and is secured in the same way. The profile of the cap may be shaped to match the 8 mm diameter of the intramedullary nail installed but could be modified to fit with other sizes.

Figure 3:
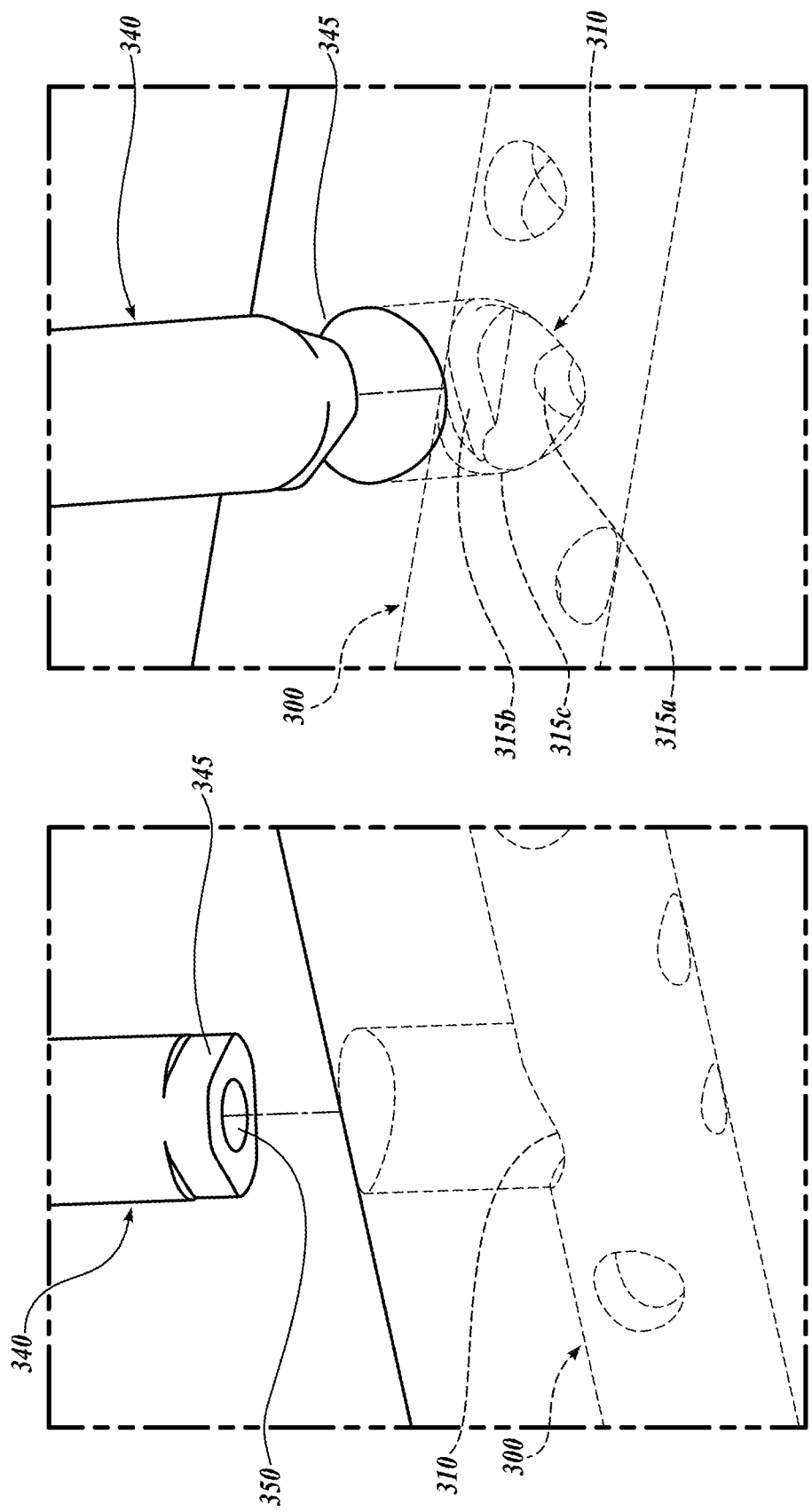
FIGS. 3A-3B are isometric views of an example intramedullary nail and locating pin in accordance with the present technology.

FIGS. 3A-3B are isometric views of an example intramedullary nail and locating pin in accordance with the present technology. FIG. 3A is a bottom view isometric view, while FIG. 3B is a top view isometric view.

Intramedullary nail 300 includes a locating hole 310. Locating hole 310 includes a first section 315a, a second section 315b, and a third section 315c. A locating pin 340, is configured 10 to fit inside the locating hole 310. In some embodiments, the locating pin 340 has a hollow portion 350. In some embodiments, the locating pin 340 is a 7 mm outer diameter tube with a 5 mm inner diameter extending just short of the end such that the head of a screw (such as screw 220 in FIG. 2) can fit through the inner channel and seat at the bottom with only the threaded portion of the screw able to fit through the last 3 mm section of the channel. In some embodiments, the first 2 mm of the locating pin is relived to fit securely into the triangular section of the locating hole. The triangular shape begins again 120 mm from the inserted end and continues to the end of the locating pin, this section is used to control the location and orientation of a guide jig (not pictured in FIGS. 3A-3B).

Figure 4:
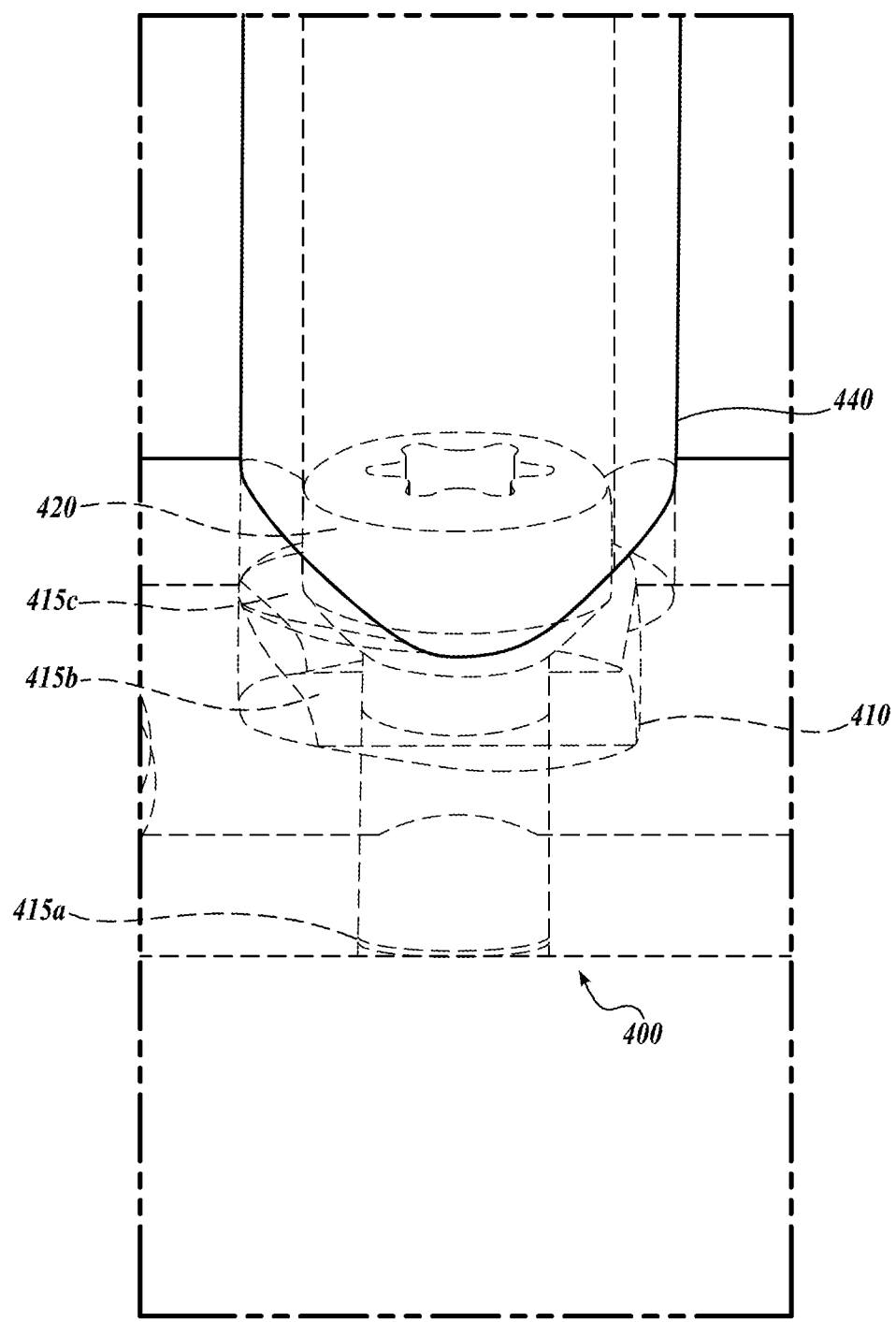
FIG. 4 is a cross-section of an example intramedullary nail and locating pin in accordance with the present technology.

FIG. 4 is a cross-section of an example intramedullary nail and locating pin in accordance with the present technology. Intramedullary nail 400 includes a locating hole 410. The locating hole 410 includes a first section 415a, a second section 415b, and a third section 415c. Attached to intramedullary nail 400 is a locating pin 440. The locator pin 440 is attached to the intramedullary nail 400 with a screw 420. In some embodiments, screw 440 is the screw 220 as illustrated in FIG. 2.

In operation, the locating pin 440 can be inserted into the locating hole 410. In some embodiments, the locating pin 440 can be rotated until it seats fully into the locating hole 410. The screw 420 can then be inserted into the hollow section of the locator pin 410, such as hollow section 350 in FIG. 3A. In some embodiments, the locator pin 410 can slide to the bottom of the pin and then be tightened so that the locator pin 410 is securely attached to the nail.

Figure 5:
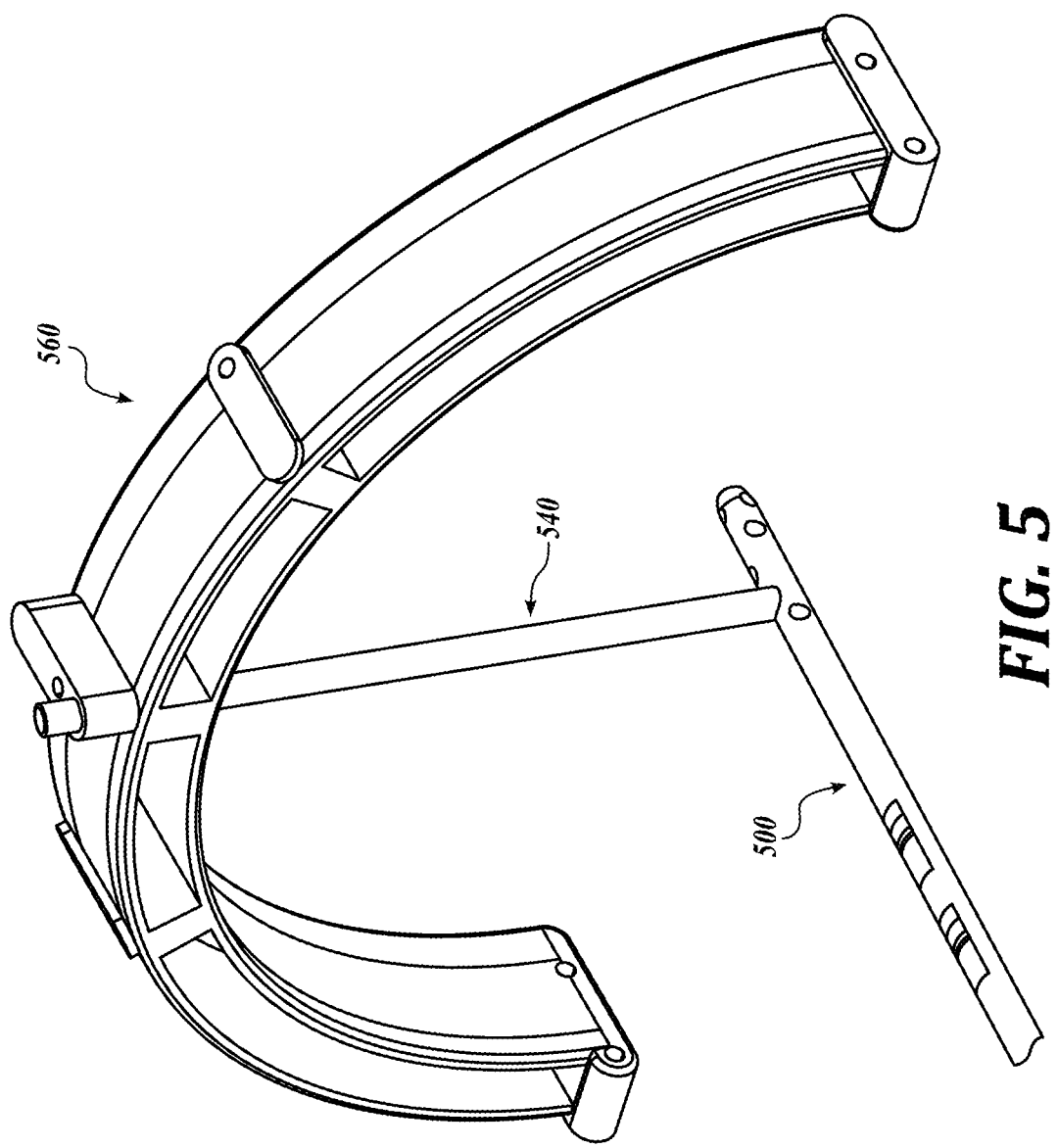
FIG. 5 is an isometric view of an example distal screw locating system in accordance with the present technology.

FIG. 5 is an isometric view of an example distal screw locating system in accordance with the present technology. In some embodiments, such as the one illustrated in FIG. 5, the distal screw locating system includes an intramedullary nail 500, a locator pin 540, and a guide jig 560. The guide jig 560 may be mounted onto the locator pin 540. The central section of guide jig 560 may have a triangular hole that fits over the locator pin 540 and rest on the bottom of the triangular section on the back end of the locator pin 540. In this position all of the holes in the guide jig 560 may precisely line up with the holes in the distal end of the intramedullary nail 500. The guide jig 560 can then be secured in this position via a small set screw that threads into a small hole located at the top of the triangular hole on the jig, and presses against the flat side of the locator pin 560.

Through the use of this system the intramedullary nail distal holes are effectively located, requiring the x-ray hole locating procedure to be performed only once rather than once for every screw. The design avoids the issues with deflection and misalignment amplification that cause other designs to fail by location on the distal end, and rigid deterministic design. This design also limits the radiation exposure to medical staff significantly as well as speeding up the procedure.

The embodiments of the invention in which an exclusive property or privilege is claimed are defined as follows:

1. A distal-screw guiding system comprising:
   an intramedullary nail;
   a locating hole at a distal end of the intramedullary nail;
   a locator pin comprised of:
   a hollow section, and
   a locating end configured to fit in the locating hole;
   a locating screw configured to securely hold the locator pin, wherein the locating screw has a domed head; and
   a jig configured to guide a user to locate at least one distal screw at the distal end of the intramedullary nail, wherein the at least one distal screw is configured to be located in a distal end of a bone
   a cap configured to fill in the locating hole when the locator pin is not in the locating hole wherein the domed head of the locating screw is configured to sit fully under a level of the cap, such that the intramedullary nail is removable without removing the cap or the locating screw.

2. The distal-screw guiding system of claim 1, wherein the locating hole is comprised of a first section, a second section, and a third section.

3. The distal-screw guiding system of claim 2, wherein the first section of the locating hole is a threaded hole through the intramedullary nail.

4. The distal-screw guiding system of claim 3, wherein the threaded hole through the intramedullary nail is through a backside of the intramedullary nail.

5. The distal-screw guiding system of claim 2, wherein the second section is a hole that extends into a midplane of the intramedullary nail.

6. The distal-screw guiding system of claim 5, wherein the second section is triangular shaped.

7. The distal-screw guiding system of claim 2, wherein the third section is a hole that extends into the intramedullary nail so that the profile of the second section is on a completely flat surface.

8. The distal-screw guiding system of claim 7, wherein the third section is circular.

9. The distal-screw guiding system of claim 1, wherein the cap is identical in shape to the locating end of the locator pin.

10. The distal-screw guiding system of claim 1, wherein the cap is shaped to match the diameter of the intramedullary nail.

11. The distal-screw guiding system of claim 1, wherein the intramedullary nail is a tibial nail.

12. The distal-screw guiding system of claim 1, wherein the intramedullary nail is a humeral nail.

13. The distal-screw guiding system of claim 1, wherein the intramedullary nail is a femoral nail.

14. A method for locating distal screws located in a distal end of a bone, the method comprising:
   placing an intramedullary nail with a distal locating hole into a bone;
   visualizing the distal locating hole with an x-ray;
   drilling a pilot hole through the bone into a small section of the distal locating hole;
   inserting a locator pin with a hollow section and a locating end into the distal locating hole, wherein the locating end is configured to fit into distal locating hole;
   inserting a locating screw into the hollow section of the locator pin so that it slides to the bottom of the locator pin, wherein the locating screw has a domed head
   tightening the locating screw so that the locator pin is attached to the intramedullary nail;
   placing a jig onto the locator pin; and
   locating at least one distal screw with the jig
   filling in the locating hole with a cap when the locator pin is not in the locating hole, wherein the domed head of the locating screw is configured to sit fully under a level of the cap, such that the intramedullary nail is removable without removing the locating screw.

15. The method of claim 14, wherein the locating hole is comprised of a first section, a second section, and a third section.

16. The method of claim 14, wherein the locator pin has a locating end.

17. The method of claim 16, wherein the locating end is triangular.

18. The method of claim 17, the method further comprising orienting one of the points of the triangular locating end of the locator pin towards the proximal end of the locator pin.

19. The method of claim 18, the method further comprising rotating the locator pin until it seats fully into the locating hole.

* * * * *